US006552240B1

(12) United States Patent
Lattner et al.

(10) Patent No.: US 6,552,240 B1
(45) Date of Patent: *Apr. 22, 2003

(54) METHOD FOR CONVERTING OXYGENATES TO OLEFINS

(75) Inventors: James R. Lattner, Seabrook, TX (US); Stephen N. Vaughn, Kingwood, TX (US); Keith H. Kuechler, Friendswood, TX (US); David C. Skouby, Centreville, VA (US); Hsiang-Ning Sun, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 189 days.

This patent is subject to a terminal disclaimer.

(21) Appl. No.: 09/708,753

(22) Filed: Nov. 8, 2000

Related U.S. Application Data

(63) Continuation-in-part of application No. 09/414,256, filed on Oct. 7, 1999, which is a continuation-in-part of application No. 08/887,766, filed on Jul. 3, 1997, now Pat. No. 6,023,005.
(60) Provisional application No. 60/135,377, filed on May 21, 1999.

(51) Int. Cl.[7] ............................... C07C 1/70; C07C 2/08

(52) U.S. Cl. ......................................... 585/639; 585/640

(58) Field of Search ........................ 585/639, 640, 585/638

(56) References Cited

U.S. PATENT DOCUMENTS

| | | | |
|---|---|---|---|
| 2,768,127 A | 10/1956 | Kimberlin, Jr. et al. | 196/55 |
| 3,785,782 A | 1/1974 | Cartmell | 23/288 S |
| 4,035,284 A | 7/1977 | Gross et al. | 208/120 |
| 4,071,573 A | 1/1978 | Owen et al. | 260/668 R |
| 4,076,796 A | 2/1978 | Reh et al. | 423/659 |
| 4,118,431 A | 10/1978 | Chen | 260/668 R |
| 4,134,926 A | 1/1979 | Tsao et al. | 260/682 |
| 4,229,608 A | 10/1980 | Chen et al. | 585/640 |
| 4,404,095 A | 9/1983 | Haddad et al. | 208/161 |
| 4,419,221 A | 12/1983 | Castagnos, Jr. et al. | 208/113 |
| 4,440,871 A | 4/1984 | Lok et al. | 502/214 |
| 4,499,327 A | 2/1985 | Kaiser | 585/640 |
| 4,513,160 A | 4/1985 | Avidan et al. | 585/640 |

(List continued on next page.)

FOREIGN PATENT DOCUMENTS

| | | | | |
|---|---|---|---|---|
| EP | 0 091 751 | 10/1983 | | C10G/3/00 |
| WO | WO 99/18055 | 4/1999 | | C07C/1/20 |

OTHER PUBLICATIONS

Blackwell et al. *Solid–State MNR of Silicoaluminophosphate Molecular Sieves and Aluminophosphate Materials*, J. Phys. Chem., vol. 92, pp. 3965–3970 (1988).

*MTO—has it time come?* Nitrogen & Methanol, No. 246, Jul.–Aug. 2000.

Barger et al., *Converting Natural Gas to Ethlyene and Propylene by the UOP/Hydro MTO Process*, 12th International Zeolite Conference 1999 Materials Research Society p. 567–573.

Chang, *Methanol Conversion to Light Olefins*, Catal. Rev.–Sci. Eng., 26(3&4), 323–345 (1984).

Kaeding et al., *Production of Chemicals from Methanol*, Journal of Catalysis 61, 155–164 (1980).

*Primary Examiner*—Bekir L. Yildirim
(74) *Attorney, Agent, or Firm*—Paul T. Lavoie; Bradley A. Keller

(57) ABSTRACT

The present invention provides a method for converting a feed containing oxygenates to olefins and comprises the following steps: providing a feed including an oxygenate; contacting the feed in a reactor apparatus with a catalyst including a molecular sieve, the contacting taking place under conditions effective to convert the oxygenate to a product including a light olefin, the conditions including a gas superficial velocity of at least two meters per second at least one point in the reaction zone; and recirculating a first portion of the catalyst to recontact the feed.

70 Claims, 1 Drawing Sheet

U.S. PATENT DOCUMENTS

| | | | |
|---|---|---|---|
| 4,552,645 A | 11/1985 | Gartside et al. | 208/80 |
| 4,664,888 A | 5/1987 | Castagnos, Jr. | 422/147 |
| 4,677,242 A | 6/1987 | Kaiser | 585/638 |
| 4,677,243 A | 6/1987 | Kaiser | 585/638 |
| 4,752,651 A | 6/1988 | Kaiser | 585/640 |
| 4,780,196 A | 10/1988 | Alagy et al. | 208/130 |
| 4,814,067 A | 3/1989 | Gartside et al. | 208/127 |
| 4,861,938 A | 8/1989 | Lewis et al. | 585/640 |
| 5,095,163 A | 3/1992 | Barger | 585/640 |
| 5,157,181 A | 10/1992 | Stine et al. | 585/329 |
| 5,191,141 A | 3/1993 | Barger et al. | 585/640 |
| 5,343,830 A | 9/1994 | Alexander et al. | 122/4 D |
| 5,714,662 A | 2/1998 | Vora et al. | 585/640 |
| 5,714,663 A | 2/1998 | Serrand et al. | 585/648 |
| 5,925,800 A | 7/1999 | Sun et al. | 585/640 |
| 5,952,538 A | 9/1999 | Vaughn et al. | 585/640 |
| 5,972,203 A | 10/1999 | Smith et al. | 208/113 |
| 6,023,005 A | 2/2000 | Lattner et al. | 585/639 |
| 6,121,503 A | 9/2000 | Janssen et al. | 585/640 |
| 6,121,504 A | 9/2000 | Kuechler et al. | 585/640 |
| 6,137,022 A | 10/2000 | Kuechler et al. | 585/638 |
| 6,166,282 A | 12/2000 | Miller | 585/638 |
| 6,174,339 B1 | 1/2001 | Varady | 55/348 |

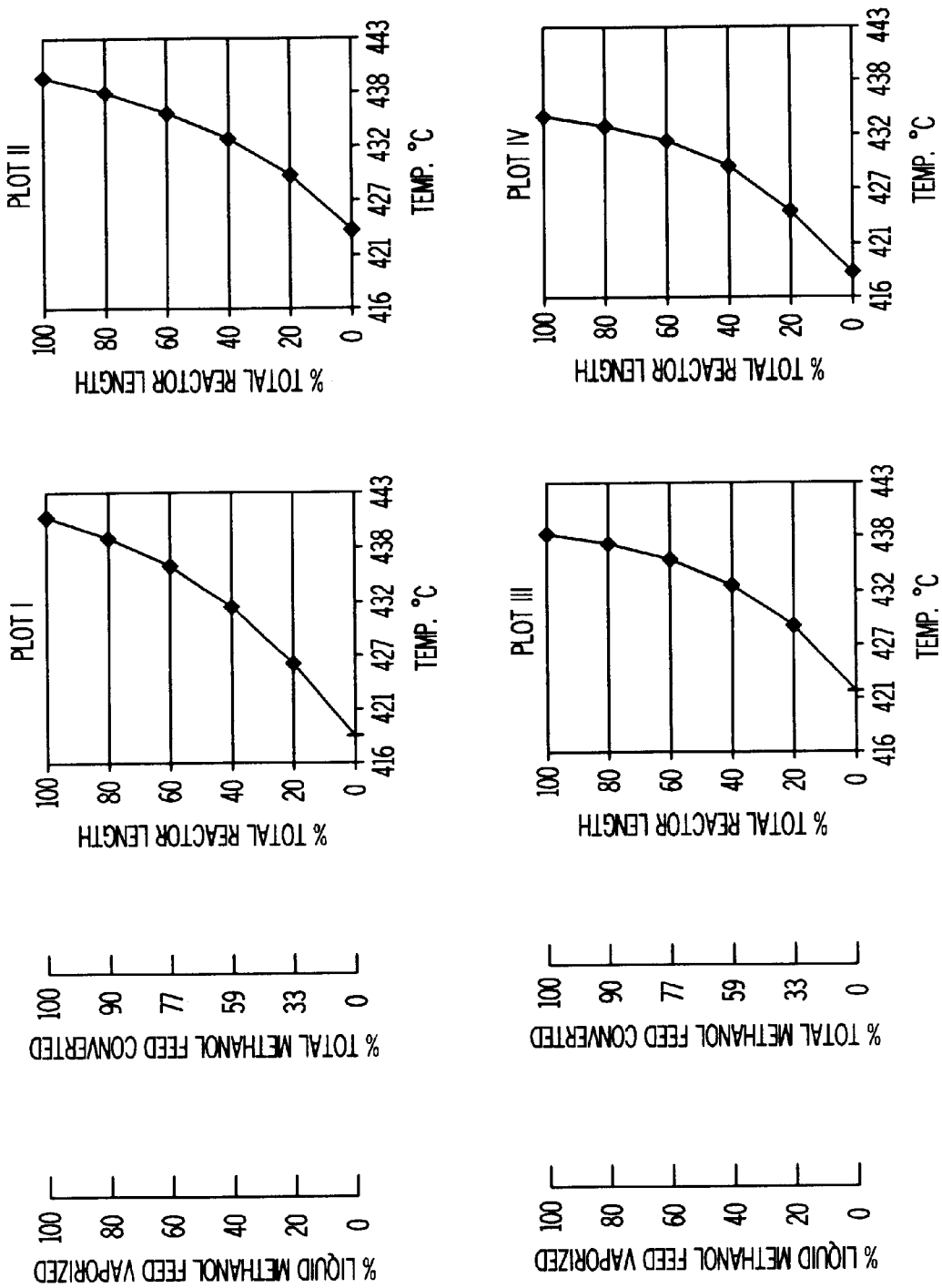
FIGURE

METHOD FOR CONVERTING OXYGENATES TO OLEFINS

CROSS REFERENCE TO RELATED APPLICATIONS

This patent application is a continuation-in-part of U.S. patent application Ser. No. 09/414,256, filed Oct. 7, 1999, which is a continuation of U.S. Provisional Patent Application No. 60/135,377 filed May 21, 1999 and which is a continuation-in-part of U.S. patent application Ser. No. 08/887,766 filed Jul. 3, 1997 which issued as U.S. Pat. No. 6,023,005.

FIELD OF THE INVENTION

The present invention relates to a method for converting a feed including an oxygenate to a product including a light olefin.

BACKGROUND OF THE INVENTION

Light olefins, defined herein as ethylene, propylene, butylene and mixtures thereof, serve as feeds for the production of numerous important chemicals and polymers. Typically, light olefins are produced by cracking petroleum feeds. Because of the limited supply of competitive petroleum feeds, the opportunities to produce low cost light olefins from petroleum feeds are limited. Efforts to develop light olefin production technologies based on alternative feeds have increased.

An important type of alternate feed for the production of light olefins is oxygenates, such as, for example, alcohols, particularly methanol and ethanol, dimethyl ether, methyl ethyl ether, diethyl ether, dimethyl carbonate, and methyl formate. Many of these oxygenates may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for light olefin production.

Because light olefins are desirable products, research has focused on methods for optimizing the yields of light olefins. Research has also focused on methods for reducing undesirable by-products, particularly light saturates such as methane and ethane, because it is expensive to separate light saturates from light olefins. For example, for ethylene recovery, a typical recovery train requires a cold box, a de-methanizer, a de-ethanizer, and an ethylene/ethane splitter.

The reaction which converts oxygenates to olefins is exothermic and contributes to an overall temperature increase in a conversion reactor apparatus. This temperature increase may cause a temperature differential in the reactor. A temperature differential results when the temperature at the portion of the reactor in which the reaction ends is higher than the temperature of the portion of the reactor in which the reaction begins. Because the product selectivities of an oxygenate to olefin conversion reaction are, at least in part, temperature dependent, the temperature increase across the reactor affects the product slate of the conversion reaction. As the temperature in the reactor increases, light saturate production increases. Various methods have been used to remove or manage the heat of reaction in order to maintain the temperature of the reaction zone in a desired range.

U.S. Pat. No. 4,071,573 to Owen et al. describes a method for effecting chemical reactions of aliphatic hetero compounds, such as alcohols, halides, mercaptans, sulfides, amines, ethers and carbonyl compounds, with a fluidized crystalline zeolite catalyst and regeneration of a portion of the catalyst used in the fluid catalyst operation. The method described in the Owen et al. patent employs a catalyst recycle to each of the catalyst contact zones. Additionally, a quench gas distributor is employed in the reactor to further control exothermic conditions in the reactor. The distribution of catalyst or quench gas to discrete reactor zones requires additional equipment and controls, both of which add to the cost and complexity of the reactor system.

Another method for maintaining temperature in the reactor is to conduct the conversion reaction at a gas superficial velocity of less than 1 meter per second. At gas superficial velocities less than about 1 meter per second, an oxygenate to olefin conversion reaction occurs at near constant temperature, i.e., isothermal conditions, due to a high degree of back mixing of both solid and gas phases in the reaction. However, as the gas superficial velocity approaches plug flow behavior, i.e. 1 m/s, the isothermal nature of the conversion reaction is lost due to a decrease in the amount of back mixing of solid and gas phases that occurs as the gas superficial velocity increases. As the solid and gas phases move through s the reactor, the temperature of the reactor increases. For example, U.S. Pat. No. 4,513,160 to Avidan describes a process for the conversion of alcohols and oxygenates to hydrocarbons in a turbulent fluid bed reactor. Avidan describes that, when using a ZSM-5 zeolite catalyst, the turbulent regime is obtained when the superficial fluid velocity is 0.5–7 feet per second (0.15–2.13 m/s). See column 7, lines 23–65.

Thus, a need exists in the art for a method useful for maintaining the desired reaction temperature, managing the heat of reaction, providing good yields of the desired product, and avoiding the production of undesirable by-products, such as light saturates and coke.

SUMMARY OF THE INVENTION

The present invention solves the current needs in the art by providing a method for converting a feed including an oxygenate to a product including a light olefin. The method of the present invention is conducted in a reactor apparatus. As used herein, the term "reactor apparatus" refers to an apparatus which includes at least a place in which an oxygenate to olefin conversion reaction takes place. As further used herein, the term "reaction zone" refers to the portion of a reactor apparatus in which the oxygenate to olefin conversion reaction takes place and is used synonymously with the term "reactor." Desirably, the reactor apparatus, includes a reaction zone, an inlet zone and a disengaging zone. The "inlet zone" is the portion of the reactor apparatus into which feed and catalyst are introduced. The "reaction zone" is the portion of the reactor apparatus in which the feed is contacted with the catalyst under conditions effective to convert the oxygenate portion of the feed into a light olefin product. The "disengaging zone" is the portion of the reactor apparatus in which the catalyst and any additional solids in the reactor are separated from the products. Typically, the reaction zone is positioned between the inlet zone and the disengaging zone.

One embodiment of the method of the present invention comprises the following steps: providing a feed including an oxygenate; contacting the feed in a reaction zone of a reactor zone of a reactor apparatus with a catalyst including a molecular sieve, the contacting taking place under conditions effective to convert the oxygenate to a product including a light olefin, the conditions including a gas superficial velocity of at least two meters per second at least one point in the reaction zone; and recirculating a first portion of the catalyst to recontact the feed.

Another embodiment of the present invention is also directed to a method for converting a feed containing an oxygenate to a light olefin. The method comprises the following steps: (a) providing a reactor apparatus having an inlet zone, a reaction zone and a disengaging zone, the reaction zone being positioned between the inlet zone and the disengaging zone; (b) feeding a feed including an oxygenate to the inlet zone; (c) contacting the feed in the reaction zone with a catalyst including a molecular sieve, the contacting taking place under conditions effective to convert the oxygenate to a product including a light olefin, the conditions including a gas superficial velocity of at least two meters per second at at least one point in the reaction zone; (d) separating the product from the catalyst in the disengaging zone; (e) recirculating a first portion of the catalyst from the disengaging zone to the inlet zone; and (f) repeating steps (b) to (e).

Yet another embodiment of the present invention is directed to a method for converting a feed including an oxygenate to a product including a light olefin through the use of a non-zeolitic molecular sieve catalyst. The method comprises the following steps: providing a feed including an oxygenate; and contacting the feed in a reaction zone of a reactor apparatus with a catalyst including a non-zeolitic molecular sieve, the contacting taking place under conditions effective to convert the oxygenate to a product including a light olefin, the conditions including a gas superficial velocity of at least one meter per second at at least one point in the reaction zone.

These and other advantages of the present invention shall become apparent from the following detailed description, the attached figure and the appended claims.

BRIEF DESCRIPTION OF THE DRAWING

The FIGURE provides a series of plots showing plots of the temperature profile along the length of the reactor for each of the cases described in the example.

DETAILED DESCRIPTION OF THE INVENTION

When converting oxygenates to a light olefin product, it is desirable to maximize the production of light olefins, and to control, typically to minimize, the production of by-products, such as light saturates and $C_5^+$ compounds. The method of the present invention accomplishes this result by providing that an oxygenate is contacted with a catalyst at a gas superficial velocity of at least one meter per second to increase the selectivity of the reaction to light olefins and to reduce the production of unwanted by-products. Additionally, in the method of the present invention, a portion of the catalyst is desirably recirculated to recontact the feed to manage the heat produced by the exothermic conversion reaction so that the temperature at which the conversion reaction is conducted can be maintained within a desired range, i.e., so that a temperature differential in the reactor can be managed. As a result, the present invention provides increased light olefins yield and decreased by-products yield.

In the process of the present invention, a feed, including an oxygenate and any diluents, is contacted in a reactor, or a reaction zone, with a catalyst at effective process conditions so as to produce a product including light olefins. These process conditions include an effective temperature, pressure, WHSV (weight hourly space velocity), gas superficial velocity and, optionally, an effective amount of diluent, correlated to produce light olefins. These process conditions are described below in detail.

One important process condition of the method of the present invention is the gas superficial velocity. As used herein and in the claims, the term, "gas superficial velocity" is defined as the combined volumetric flow rate of vaporized feedstock, including diluent which can be present in the feedstock, and conversion products, divided by the cross-sectional area of the reaction zone. Because the oxygenate is converted to a product including a light olefin while flowing through the reaction zone, the gas superficial velocity may vary at different locations within the reaction zone depending on the total number of moles of gas present and the cross section of a particular location in the reaction zone, temperature, pressure and other relevant reaction parameters. In one embodiment of the present invention, the gas superficial velocity is maintained at a rate of greater than 1 meter per second (m/s) at at least one point in the reaction zone. Desirably, the gas superficial velocity is greater than about 2 m/s at at least one point in the reaction zone. More desirably, the gas superficial velocity is greater than about 2.5 m/s at at least one point in the reaction zone. Even more desirably, the gas superficial velocity is greater than about 4 m/s at at least one point in the reaction zone. Most desirably, the gas superficial velocity is greater than about 8 m/s at at least one point in the reaction zone. More desirably with the present inventor, the gas superficial velocity is maintained constant in the reaction zone such that the gas superficial velocity is maintained at a rate greater than 1 m/s at all points in the reaction zone. Desirably, the gas superficial velocity is greater than about 2 m/s at all points in the reaction zone. More desirably, the gas superficial velocity is greater than about 2.5 m/s at all points in the reaction zone. Even more desirably, the gas superficial velocity is greater than about 4 m/s at all points in the reaction zone. Most desirably, the gas superficial velocity is greater than about 8 m/s at all points in the reaction zone.

Maintaining the gas superficial velocity at these rates increases the approach to plug flow behavior of the gases flowing in the reactor. As the gas superficial velocity increases above 1 m/s, a reduction in axial diffusion or backmixing of the gases results from a reduction in internal recirculation of solids, which carry gas with them. (Ideal plug flow behavior occurs when elements of the homogeneous fluid reactant move through a reactor as plugs moving parallel to the reactor axis). Minimizing the backmixing of the gases in the reactor increases the selectivity to the desired light olefins in the oxygenate conversion reaction.

When the gas superficial velocity approaches 1 m/s or higher, a substantial portion of the catalyst in the reactor may be entrained with the gas exiting the reactor. Thus, in order to maintain at least near plug flow gas behavior and near isothermal conditions in the reactor, the method of the present invention may also employ recirculation of a portion of the catalyst exiting the reactor to recontact the feed. This recirculation may occur either within the reactor apparatus or outside the reactor apparatus.

The mass of recirculating catalyst is used to control the temperature differential in the reactor by absorbing a portion of the heat generated by the conversion reaction. The temperature is controlled by controlling the amount of catalyst which is recirculated. For the present invention, "temperature differential" is defined as the change in temperature from the inlet zone to the outlet of the reactor. The "outlet" is the portion of the reactor at which the reactants (feed, catalyst and products) pass from the reactor to the disengaging zone. The temperature of the inlet zone is calculated by balancing the heat content of the total catalyst plus non-reactive solids and the total vapor fed to the inlet zone. Any sensible heat effects of the liquid feed itself are ignored in the calculation of the temperature of the inlet zone or of any other part of the reactor, and only the heat of vaporization is considered once it enters the reactor, in addition to the sensible heat impacts from the vapors produced from the liquid feed. The assumption is made that a negligible conversion of oxygenate occurs and, hence, negligible heat of reaction at the inlet zone is generated, and conversion and heat of reaction only occur to any significant extent in the reactor when the oxygenate has become a vapor.

In this invention, the temperature differential in the reaction zone (reactor) is desirably maintained at less than about 100° C., which is defined herein to be the upper temperature limit of "near isothermal conditions." More desirably, the temperature differential is maintained at less than about 50° C. Most desirably, the temperature differential is maintained at less than about 30° C. It is desirable to maintain a low temperature differential as possible in order to create conditions which are as close to near isothermal as practical in the reaction zone (reactor).

Desirably, the rate of catalyst, comprising molecular sieve and any other materials such as binders, fillers, etc., recirculated to recontact the feed is from about 1 to about 100 times, more desirably from about 10 to about 80 times, and most desirably from about 10 to about 50 times the total feed rate of oxygenates to the reactor. Desirably, a portion of the catalyst, comprising molecular sieve and any other materials such as binders, fillers, etc., is removed from the reactor for regeneration and recirculation back to the reactor at a rate of from about 0.1 times to about 10 times, more desirably from about 0.2 to about 5 times, and most desirably from about 0.3 to about 3 times the total feed rate of oxygenates to the reactor.

Desirably, the catalyst, comprising molecular sieve and any other materials such as binders, fillers, etc. should have a heat capacity of from about 0.1 to about 1 cal/g-° C., more preferably from about 0.1 to about 0.8 call g-° C., and most preferably from about 0.2 to about 0.5 cal/g-° C.

The temperature useful to convert oxygenates to light olefins varies over a wide range depending, at least in part, on the catalyst, the fraction of regenerated catalyst in a catalyst mixture, and the configuration of the reactor apparatus and the reactor. Although the present invention is not limited to a particular temperature, best results are obtained if the process is conducted at a temperature from about 200° C. to about 700° C., desirably from about 250° C. to about 600° C., and most desirably from about 300° C. to about 500° C. Lower temperatures generally result in lower rates of reaction, and the formation rate of the desired light olefin products may become markedly slower. However, at temperatures greater than 700° C., the process may not form an optimum amount of light olefin products, and the rate at which coke and light saturates form on the catalyst may become too high.

Light olefins will form—although not necessarily in optimum amounts—at a wide range of pressures including, but not limited to, autogeneous pressures and pressures from about 0.1 kPa to about 5 MPa. A desired pressure is from about 5 kPa to about 1 MPa and most desirably from about 20 kPa to about 500 kPa. The foregoing pressures do not include that of a diluent, if any, and refer to the partial pressure of the feed as it relates to oxygenate compounds and/or mixtures thereof. Pressures outside of the stated ranges may be used and are not excluded from the scope of the invention. Lower and upper extremes of pressure may adversely affect selectivity, conversion, coking rate, and/or reaction rate; however, light olefins will still form and, for that reason, these extremes of pressure are considered part of the present invention.

The process of the present invention is continued for a period of time sufficient to produce the desired light olefins. A steady state or semi-steady state production of light olefins may be attained during this period of time, largely determined by the reaction temperature, the pressure, the catalyst selected, the amount of recirculated spent catalyst, the level of regeneration, the weight hourly space velocity, the superficial velocity, and other selected process design characteristics.

A wide range of WHSV's for the oxygenate conversion reaction, defined as weight of total oxygenate to the reaction zone per hour per weight of molecular sieve in the catalyst in the reaction zone, function with the present invention. The total oxygenate to the reaction zone includes all oxygenate in both the vapor and liquid phase. Although the catalyst may contain other materials which act as inerts, fillers or binders, the WHSV is calculated using only the weight of molecular sieve in the catalyst in the reaction zone. The WHSV is desirably high enough to maintain the catalyst in a fluidized state under the reaction conditions and within the reactor configuration and design. Generally, the WHSV is from about 1 hr$^{-1}$ to about 5000 hr$^{-1}$, desirably from about 2 hr$^{-1}$ to about 3000 hr$^{-1}$, and most desirably from about 5 hr$^{-1}$ to about 1500 hr$^{-1}$. The applicants have discovered that operation of the oxygenate to olefin conversion reaction at a WHSV greater than 20 hr$^{-1}$ reduces the methane content in the product slate of the conversion reaction. Thus, the conversion reaction is desirably operated at a WHSV of at least about 20 hr$^{-1}$. For a feed comprising methanol, dimethyl ether, or mixtures thereof, the WHSV is desirably at least about 20 hr$^{-1}$ and more desirably from about 20 hr$^{-1}$ to about 300 hr$^{-1}$.

It is particularly preferred that the reaction conditions for making olefins from an oxygenate comprise a WHSV of at least about 20 hr$^{-1}$ and a Temperature Corrected Normalized Methane Selectivity (TCNMS) of less than about 0.016. As used herein, TCNMS is defined as the Normalized Methane Selectivity (NMS) when the temperature is less than 400° C. The NMS is defined as the methane product yield divided by the ethylene product yield wherein each yield is measured on or is converted to a weight % basis. When the temperature is 400° C. or greater, the TCNMS is defined by the following equation, in which T is the average temperature within the reactor in ° C.:

$$TCNMS = \frac{NMS}{1 + (((T-400)/400) \times 14.84)}.$$

Oxygenate conversion should be maintained sufficiently high to avoid the need for commercially unacceptable levels of feed recycling. While 100% oxygenate conversion is desired for the purpose of completely avoiding feed recycle, a reduction in unwanted by-products is observed frequently when the conversion is about 98% or less. Since recycling up to as much as about 50% of the feed can be commercially acceptable, conversion rates from about 50% to about 98% are desired. Conversion rates may be maintained in this range—50% to about 98%—using a number of methods familiar to persons of ordinary skill in the art. Examples include, but are not necessarily limited to, adjusting one or more of the following: reaction temperature; pressure; flow rate (weight hourly space velocity and/or gas superficial velocity); catalyst recirculation rate; reactor apparatus configuration; reactor configuration; feed composition; amount of liquid feed relative to vapor feed (as will be discussed below); amount of recirculated catalyst; degree of catalyst regeneration; and other parameters which affect the conversion.

During the conversion of oxygenates to light olefins, carbonaceous deposits accumulate on the catalyst used to promote the conversion reaction. At some point, the build up of these carbonaceous deposits causes a reduction in the capability of the catalyst to convert the oxygenate feed to light olefins. At this point, the catalyst is partially deactivated. When a catalyst can no longer convert an oxygenate to an olefin product, the catalyst is considered to be fully deactivated. As an optional step in the process of the present invention, a portion of the catalyst is withdrawn from the reactor apparatus and at least a portion of the portion removed from the reactor is partially, if not fully, regenerated in a regenerator. By regeneration, it is meant that the carbonaceous deposits are at least partially removed from the catalyst. Desirably, the portion of the catalyst withdrawn from the reactor is at least partially deactivated. The remaining portion of the catalyst in the reactor apparatus is recirculated without regeneration. The regenerated catalyst, with or without cooling, is then returned to the reactor. Desirably, the rate of withdrawing the portion of the catalyst for regeneration is from about 0.1% to about 99% of the rate of the catalyst exiting the reactor. More desirably, the rate is from about 0.2% to about 50%, and, most desirably, from about 0.5% to about 5%.

Desirably, a portion of the catalyst, comprising molecular sieve and any other materials such as binders, fillers, etc., is removed from the reactor for regeneration and recirculation back to the reactor at a rate of from about 0.1 times to about 10 times, more desirably from about 0.2 to about 5 times, and most desirably from about 0.3 to about 3 times the total feed rate of oxygenates to the reactor. These rates pertain to the catalyst containing molecular sieve only, and do not include non-reactive solids. The rate of total solids, i.e., catalyst and non-reactive solids, removed from the reactor for regeneration and recirculation back to the reactor will vary these rates in direct proportion to the content of non-reactive solids in the total solids.

Desirably, the catalyst regeneration is carried out in the presence of a gas comprising oxygen or other oxidants. Examples of other oxidants include, but are not necessarily limited to, singlet $O_2$, $O_3$, $SO_3$, $N_2O$, NO, $NO_2$, $N_2O_5$, and mixtures thereof. Air and air diluted with nitrogen or $CO_2$ are desired regeneration gases. The oxygen concentration in air can be reduced to a controlled level to minimize overheating of, or creating hot spots in, the regenerator. The catalyst may also be regenerated reductively with hydrogen, mixtures of hydrogen and carbon monoxide, or other suitable reducing gases.

The catalyst may be regenerated in any number of methods—batch, continuous, semi-continuous, or a combination thereof. Continuous catalyst regeneration is a desired method. Desirably, the catalyst is regenerated to a level of remaining coke from about 0.01 wt % to about 15 wt % of the weight of the catalyst.

The catalyst regeneration temperature should be from about 250° C. to about 750° C., and desirably from about 500° C. to about 700° C. Because the regeneration reaction takes place at a temperature considerably higher than the oxygenate conversion reaction, it may be desirable to cool at least a portion of the regenerated catalyst to a lower temperature before it is sent back to the reactor. A heat exchanger located external to the regenerator may be used to remove some heat from the catalyst after it has been withdrawn from the regenerator. When the regenerated catalyst is cooled, it is desirable to cool it to a temperature which is from about 200° C. higher to about 200° C. lower than the temperature of the catalyst withdrawn from the reactor. More desirably, it is cooled to a temperature from about 10° C. to about 200° C. lower than the temperature of the catalyst withdrawn from the reactor. This cooled catalyst then may be returned to either some portion of the reactor apparatus, the catalyst regenerator or both. When the regenerated catalyst from the regenerator is returned to a reactor apparatus, it may be returned to the disengaging zone, the reaction zone, and/or the inlet zone. It may also be returned to a conduit which recirculates the catalyst from the disengaging zone to the inlet zone. Direct or indirect introduction of the cooled catalyst into the reactor or regenerator serves to reduce the average temperature in the reactor or regenerator.

Desirably, catalyst regeneration is carried out at least partially deactivated catalyst that has been stripped of most of readily removable organic materials (organics) in a stripper or stripping chamber first. This stripping can be achieved by passing a stripping gas over the spent catalyst at an elevated temperature. Gases suitable for stripping include steam, nitrogen, helium, argon, methane, $CO_2$, CO, hydrogen, and mixtures thereof. A preferred gas is steam. Gas hourly space velocity (GHSV, based on volume of gas to volume of catalyst and coke) of the stripping gas is from about 0.1 $h^{-1}$ to about 20,000 $h^{-1}$. Acceptable temperatures of stripping are from about 250° C. to about 750° C., and desirably from about 350° C. to about 675° C.

The process of the present invention for converting oxygenates to light olefins employs a feed including an oxygenate. As used herein, the term "oxygenate" is defined to include, but is not necessarily limited to, hydrocarbons containing oxygen such as the following: aliphatic alcohols, ethers, carbonyl compounds (aldehydes, ketones, carboxylic acids, carbonates, and the like), and mixtures thereof. The aliphatic moiety desirably should contain in the range of from about 1–10 carbon atoms and more desirably in the range of from about 1–4 carbon atoms. Representative oxygenates include, but are not necessarily limited to, lower straight chain or branched aliphatic alcohols, and their unsaturated counterparts. Examples of suitable oxygenates include, but are not necessarily limited to the following: methanol; ethanol; n-propanol; isopropanol; $C_4$–$C_{10}$ alcohols; methyl ethyl ether; dimethyl ether; diethyl ether; di-isopropyl ether; methyl formate; formaldehyde; di-methyl carbonate; methyl ethyl carbonate; acetone; and mixtures thereof. Desirably, the oxygenate used in the conversion reaction is selected from the group consisting of methanol, dimethyl ether and mixtures thereof More desirably the oxygenate is methanol. The total charge of feed to the reactor apparatus may contain additional components, such as diluents.

One or more diluents may be fed to the reaction zone with the oxygenates, such that the total feed mixture comprises diluent in a range of from about 1 mol % and about 99 mol %. Diluents which may be employed in the process include, but are not necessarily limited to, helium, argon, nitrogen, carbon monoxide, carbon dioxide, hydrogen, water, paraffins, other hydrocarbons (such as methane), aromatic compounds, and mixtures thereof. Desired diluents include, but are not necessarily limited to, water and nitrogen.

The catalyst suitable for catalyzing the oxygenate-to-olefin conversion reaction of the present invention includes a molecular sieve and mixtures of molecular sieves. Molecular sieves can be zeolitic (zeolites) or non-zeolitic (non-zeolites). Useful catalysts may also be formed from mixtures of zeolitic and non-zeolitic molecular sieves. Desirably, the catalyst includes a non-zeolitic molecular sieve. Desired molecular sieves for use with the process of the present invention include "small" and "medium" pore molecular sieves. "Small pore" molecular sieves are defined as molecular sieves with pores having a diameter of less than about 5.0 Angstroms. "Medium pore" molecular sieves are defined as molecular sieves with pores having a diameter from about 5.0 to about 10.0 Angstroms.

Useful zeolitic molecular sieves include, but are not limited to, mordenite, chabazite, erionite, ZSM-5, ZSM-34, ZSM-48 and mixtures thereof. Methods of making these molecular sieves are known in the art and need not be discussed here. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the Atlas of Zeolite Structural Types, W. M. Meier and D. H. Olsen, Butterworth Heineman, 3rd ed., 1997, the detailed description of which is explicitly incorporated herein by reference.

Silicoaluminophosphates ("SAPOs") are one group of non-zeolitic molecular sieves that are useful in the present invention. SAPOs comprise a three-dimensional microporous crystal framework structure of $[SiO_2]$, $[AlO_2]$ and $[PO_2]$ tetrahedral units. The way Si is incorporated into the structure can be determined by $^{29}Si$ MAS NMR. See Blackwell and Patton, J. Phys. Chem., 92, 3965 (1988). The desired SAPO molecular sieves will exhibit one or more peaks in the $^{29}Si$ MAS NMR, with a chemical shift [(Si)] in the range of –88 to –96 ppm and with a combined peak area in that range of at least 20% of the total peak area of all peaks with a chemical shift [(Si)] in the range of –88 ppm to –115 ppm, where the [(Si)] chemical shifts refer to external tetramethylsilane (TMS).

It is desired that the silicoaluminophosphate molecular sieve used in this invention have a relatively low $Si/Al_2$ ratio. In general, the lower the $Si/Al_2$ ratio, the lower the $C_1$–$C_4$ saturates selectivity, particularly propane selectivity. A $Si/Al_2$ ratio of less than 0.65 is desirable, with a $Si/Al_2$ ratio of not greater than 0.40 being preferred, and a $SiAl_2$ ratio of not greater than 0.32 being particularly preferred. A $Si/Al_2$ ratio of not greater than 0.20 is most preferred.

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size ranging from about 3.5 to 5 angstroms, more preferably from 4.0 to 5.0 angstroms. These pore sizes are typical of molecular sieves having 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphoruscontaining compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

Additional olefin-forming molecular sieve materials can be mixed with the silicoaluminophosphate catalyst if desired. Several types of molecular sieves exist, each of which exhibit different properties. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. Preferred molecular sieves which can be combined with a silicoaluminophosphate catalyst include ZSM-5, ZSM-34, erionite, and chabazite.

Substituted SAPOs form a class of molecular sieves known as "MeAPSOs," which are also useful in the present invention. Processes for making MeAPSOs are known in the art. SAPOs with substituents, such as MeAPSOs, also may be suitable for use in the present invention. Suitable substituents, "Me," include, but are not necessarily limited to, nickel, cobalt, manganese, zinc, titanium, strontium, magnesium, barium, and calcium. The substituents may be incorporated during synthesis of the MeAPSOs. Alternately, the substituents may be incorporated after synthesis of SAPOs or MeAPSOs using many methods. These methods include, but are not necessarily limited to ion-exchange, incipient wetness, dry mixing, wet mixing, mechanical mixing, and combinations thereof.

Desired MeAPSOs are small pore MeAPSOs having pore size smaller than about 5 Angstroms. Small pore MeAPSOs include, but are not necessarily limited to, NiSAPO-34, CoSAPO-34, NiSAPO-17, CoSAPO-17, and mixtures thereof.

Aluminophosphates (ALPOs) with substituents, also known as "MeAPOs," are another group of molecular sieves that may be suitable for use in the present invention, with desired MeAPOs being small pore MeAPOs. Processes for making MeAPOs are known in the art. Suitable substituents include, but are not necessarily limited to nickel, cobalt, manganese, zinc, titanium, strontium, magnesium, barium, and calcium. The substituents may be incorporated during synthesis of the MeAPOs. Alternately, the substituents may be incorporated after synthesis of ALPOs or MeAPOs using many methods. The methods include, but are not necessarily limited to ion-exchange, incipient wetness, dry mixing, wet mixing, mechanical mixing, and combinations thereof.

The molecular sieve may also be incorporated into a solid composition, preferably solid particles, in which the molecular sieve is present in an amount effective to catalyze the desired conversion reaction. The solid particles may include a catalytically effective amount of the molecular sieve and matrix material, preferably at least one of a filler material and a binder material, to provide a desired property or properties, e.g., desired catalyst dilution, mechanical strength and the like, to the solid composition. Such matrix materials are often to some extent porous in nature and often have some nonselective catalytic activity to promote the formation of undesired products and may or may not be effective to promote the desired chemical conversion. Such matrix, e.g., filler and binder, materials include, for example, synthetic and naturally occurring substances, metal oxides, clays, silicas, aluminas, silica-aluminas, silica-magnesias, silica-zirconias, silica-thorias, silica-beryllias, silica-titanias, silica-alumina-thorias, silica-aluminazirconias, and mixtures of these materials.

The solid catalyst composition preferably comprises about 1% to about 99%, more preferably about 5% to about 90%, and still more preferably about 10% to about 80%, by weight of molecular sieve; and an amount of about 1% to about 99%, more preferably about 5% to about 90%, and still more preferably about 10% to about 80%, by weight of matrix material.

The preparation of solid catalyst compositions, e.g., solid particles, comprising the molecular sieve and matrix material, is conventional and well known in the art and, therefore, is not discussed in detail here.

The catalyst may further contain binders, fillers, or other material to provide better catalytic performance, attrition resistance, regenerability, and other desired properties. Desirably, the catalyst is fluidizable under the reaction conditions. The catalyst should have particle sizes of from about $20\mu$ to about $3,000\mu$, desirably from about $30\mu$ to about $200\mu$, and more desirably from about $50\mu$ to about $150\mu$. The catalyst may be subjected to a variety of treatments to achieve the desired physical and chemical characteristics. Such treatments include, but are not necessarily limited to, calcination, ball milling, milling, grinding, spray drying, hydrothermal treatment, acid treatment, base treatment, and combinations thereof.

As additional methods for controlling the heat generated by the conversion reaction and, subsequently, the temperature differential in the reactor, the present invention may include one or more or all of the following steps: providing a portion of the oxygenate portion of the feed to the reactor in a liquid form; providing at least a portion of the diluent to the reactor in a liquid form; and providing non-reactive solids to the reactor apparatus.

When a portion of the feed is provided in a liquid form, the liquid portion of the feed may be either oxygenate, diluent or a mixture of both. The liquid portion of the feed may be directly injected into the reactor, or entrained or otherwise carried into the reactor with the vapor portion of the feed or a suitable carrier gas/diluent. By providing a portion of the feed (oxygenate and/or diluent) in the liquid phase, the temperature differential in the reactor can be further controlled. The exothermic heat of reaction of oxygenate conversion is partially absorbed by the endothermic heat of vaporization of the liquid portion of the feed. Controlling the proportion of liquid feed to vapor feed fed to the reactor thus allows control of the temperature differential in the reactor. Introduction of liquid feed to the reactor acts in concert with the recirculation of catalyst and non-reactive solids, providing another independent variable to improve overall control of the temperature differential in the reactor.

The amount of feed provided in a liquid form, whether fed separately or jointly with the vapor feed, is from about 0.1 wt. % to about 85 wt. % of the total oxygenate content plus diluent in the feed. More desirably, the range is from about 1 wt. % to about 75 wt. % of the total oxygenate plus diluent feed, and most desirably the range is from about 5 wt. % to about 65 wt. %. The liquid and vapor portions of the feed may be the same composition, or may contain varying proportions of the same or different oxygenates and same or different diluents. One particularly effective liquid diluent is water, due to its relatively high heat of vaporization, which allows for a high impact on the reactor temperature differential with a relatively small rate. Other useful diluents are described above. Proper selection of the temperature and pressure of any appropriate oxygenate and/or diluent being fed to the reactor will ensure at least a portion is in the liquid phase as it enters the reactor and/or comes into contact with the catalyst or a vapor portion of the feed and/or diluent.

Optionally, the liquid fraction of the feed may be split into portions and introduced to the inlet zone and at a multiplicity of locations along the length of the reactor. This may be done with either the oxygenate feed, the diluent or both. Typically, this is done with the diluent portion of the feed. Another option is to provide a nozzle which introduces the total liquid fraction of the feed to the inlet zone or reactor in a manner such that the nozzle forms liquid droplets of an appropriate size distribution which, is when entrained with the gas and solids introduced to the inlet zone or reactor, vaporize gradually along the length of the reactor. Either of these arrangements or a combination thereof may be used to better control the temperature differential in the reactor. The means of introducing a multiplicity of liquid feed points in a reactor or designing a liquid feed nozzle to control droplet size distribution is well known in the art and is not discussed here.

Non-reactive solids which contain no molecular sieve may be mixed with the catalyst solids, and used in the reactor, and recirculated to the reactor and regenerator. These non-reactive solids have the same capability as the catalyst to provide inertial mass to control the heat generated by the conversion reaction, but are substantially inert for the purposes of oxygenate conversion. Suitable materials for use as non-reactive solids are metals, metal oxides, and mixtures thereof. Particularly suitable materials are those used as matrices for the catalyst formulation, e.g., fillers and binders such as silicas and aluminas, among others, and mixtures thereof. Desirably, the non-reactive solids should have a heat capacity of from about 0.05 to about 1 cal/g-° C., more preferably from about 0.1 to about 0.8 cal/g-° C., and most preferably from about 0.1 to about 0.5 call g-° C. Further, desirably, the mass proportion of non-reactive solids to catalyst is from about 0.01 to about 10, more desirably from about 0.05 to about 5.

Desirably, the rate of catalyst, comprising molecular sieve and any other materials such as binders, fillers, etc., plus non-reactive solids, recirculated to recontact the feed is from about 1 to about 100 times, more desirably from about 10 to about 80 times, and most desirably from about 10 to about 50 times the total feed rate of oxygenates to the reactor.

One skilled in the art will appreciate that the non-reactive solids may also be regenerated with the catalyst in the manner described above.

The process of the present invention is desirably carried out in a reactor apparatus which comprises an inlet zone, a reaction zone, and a disengaging zone. When the process of the present invention is conducted in this type of reactor apparatus, at least a portion of the catalyst/solids is recirculated from the disengaging zone to the inlet zone to maintain the reactor at near isothermalconditions. At least a portion of the vapor feed then mixes with the catalyst/solids in the inlet zone and is directed to the reaction zone in which the oxygenate to olefin conversion reaction takes place. Optionally, a liquid feed and/or diluent portion of the total feed or various sub-portions thereof may be directed to the inlet zone and/or to one or more locations in the reaction zone. With this apparatus, the catalyst/solids can be recirculated either inside the reactor apparatus or external to the rector apparatus as the catalyst/solids are recirculated from the disengaging zone to the inlet zone and/or the reaction zone. As also described, an additional portion of the catalyst/solids can optionally be removed from the reactor apparatus and sent to a regenerator to regenerate the catalyst. Catalyst/solids from the regenerator can be returned to any of the three zones, or may be directed to a conduit which serves to recirculate the catalyst/solids from the disengaging zone to the inlet zone or reaction zone.

The following example is presented as being illustrative of the present invention and are not intended to limit the present invention in any manner.

EXAMPLE

A reactor apparatus of the present invention is designed and operated with a gas superficial velocity of 2 meters per second, introducing a substantial plug flow characteristic to the gas flowing in the reactor with accompanying temperature differential between the reactor inlet and outlet zones. A substantial portion of catalyst and solids from the outlet zone are. recirculated to the inlet zone, along with catalyst and solids from a regenerator.

Referring to Table 1, varying amounts substantially pure liquid and vapor methanol feed, substantially pure liquid and vapor water, catalyst and non-reactive solids are introduced to the inlet zone of the reactor apparatus under varied conditions, Cases I–VI. The corresponding resultant state of the mixed materials at the entrance to the reactor, the inlet zone temperature, is also shown. Those entrance conditions are determined by ignoring the heat capacity of the liquid methanol feed since the reactor apparatus is designed to provide vaporization all along the length of the reactor, while allowing that the vapor and solid more or less instantaneously reach a common, equilibrated temperature based on the prevailing heat balance using the properties shown in Table 2. Finally, the combined state of the materials at the reactor outlet related to the inlet zone conditions for the six cases is provided, again calculating the heat balance using the properties in Table 3. In all cases the reactor pressure balance is identical, and the reaction proceeds to consume 100% of the methanol.

For each of the cases, a plot of the temperature profile along the length of the reactor is shown in the Figure. For each plot, the point of 0% Total Reactor Length is the reactor inlet zone, and the point of 100% Total Reactor Length is the reactor outlet zone, described above. For each case, it is allowed that the reactor design provides for identical extents of conversion and liquid methanol feed vaporization along the Reactor Length as shown in FIG. 1.

For Case I/Plot I, 100% of the methanol feed is in the vapor form. The temperature differential is 42° F.

For Case II/Plot II, the reactor conditions are all the same as in Case I except that the rate of recirculated catalyst solids is increased by 50% over Case I. The levels of methanol conversion are maintained the same as in Case I by increasing the proportion of binder and filler in the circulated catalyst solid, such that the rate of active molecular sieve to the reactor is kept constant. Note that the temperature differential is now 28° F., showing that the method of this invention controlling catalyst recirculation will control the approach to isothermal operation in the reactor, in this case providing a more isothermal operation than Case I.

For Case III/Plot III the reactor conditions are all the same as in Case I except that the methanol feed is changed such that 24% is in the liquid form. The temperature differential is now 30° F., showing that the method of this invention controlling the proportion of feed to the reactor in the liquid form will control the approach to isothermal operation in the reactor, in this case providing a more isothermal operation than Case I.

For Case IV/Plot IV the reactor conditions are all the same as in Case I except that an amount of liquid water of about 12% of the total rate of methanol feed is provided to the inlet zone. The temperature differential is now 30° F., showing that the method of this invention controlling the proportion of total liquid to the reactor will control the approach to isothermal operation in the reactor, in this case providing a more isothermal operation than Case I.

For Case V/Plot V the reactor conditions are all the same as in Case I except that an amount of inert solids at about 25% the rate of the catalyst rate in Case I are circulated along with the catalyst. The solids are designed to have about the same properties as the catalyst in terms of particle size, heat capacity, density, etc. The temperature differential is now 34° F., showing that the method of this invention controlling inert solids catalyst recirculation will control the approach to isothermal operation in the reactor, in this case providing a more isothermal operation than Case I.

For Case VI/Plot VI the reactor conditions are all the same as in Case I except both that the rate of recirculated catalyst solids is increased by 25% over Case I, and about 12% of the feed methanol is provided in the liquid form. The levels of methanol conversion are maintained the same as in Case I by increasing the proportion of binder and filler in the circulated catalyst solid, such that the rate of active molecular sieve to the reactor is kept constant. The temperature differential is now 29° F., showing that the method of this invention controlling catalyst recirculation in conjunction with controlling the proportion of feed in the liquid form will control the approach to isothermal operation in the reactor, in this case providing a more isothermal operation than Case I.

In addition to polyolefins, numerous other olefin derivatives may be formed from the olefins produced by the conversion reaction of the present invention or olefins

TABLE 1

| Apparatus | | Pres. | Case I Base Case | | Case II Cat. Circ. | | Case III Liq. MeOH | | Case IV Liq. Water | | Case V Non-react Solids | | Case III Cat. Circ. & Liq. MeOH | |
|---|---|---|---|---|---|---|---|---|---|---|---|---|---|---|
| Area | Material/State | Psia | Klb/hr | °F. | Klb/hr | °F. | Klb/hr | °F. | Klb/hr | °F. | Klb/hr | °F. | Klb/hr | °F. |
| Inlet Zone | Methanol/Vapor | 45 | 1,045 | 207 | 1,045 | 207 | 794 | 207 | 1,045 | 207 | 1,045 | 207 | 920 | 207 |
| | Methanol/Liquid | 45 | — | — | — | — | 251 | 207 | — | — | — | — | 125 | 207 |
| | Water/Vapor | 45 | — | — | — | — | — | — | — | — | — | — | — | — |
| | Water/Liquid | 45 | — | — | — | — | — | — | 125 | 207 | — | — | — | — |
| | Catalyst/Solid | 45 | 33,800 | 815 | 50,700 | 815 | 33,800 | 815 | 33,800 | 815 | 33,800 | 815 | 42,250 | 815 |
| | Non-reactive/Solid | 45 | — | — | — | — | — | — | — | — | 8,450 | 815 | — | — |
| | Combined (Inlet Zone Temperature) | 45 | 34,845 | 784 | 51,745 | 794 | 34,845 | 791 | 34,970 | 784 | 43,295 | 790 | 43,295 | 793 |
| Reactor Outlet | Combined | 42 | 34,845 | 826 | 51,745 | 823 | 34,845 | 821 | 34,970 | 814 | 43,295 | 824 | 43,295 | 822 |
| Temperature Differential | | | | | | 42 | | 29 | | 30 | | 30 | | 34 | | 29 |

TABLE 2

Properties of materials in Example 1

| | Heat Capacity Btu/lb-°F. | Heat of Vaporization Btu/lb | Heat of Reaction Btu/lb (exothermic) |
|---|---|---|---|
| Liquid Water | not applicable | 935.0 | not applicable |
| Vapor Water | 0.500 | not applicable | not applicable |
| Liquid Methanol | not applicable | 506.0 | not applicable |
| Vapor Methanol | 0.464 | not applicable | 388.4 |
| Solid Catalyst | 0.270 | not applicable | not applicable |
| Solid Non-reactive | 0.270 | not applicable | not applicable |
| Reaction Product | 0.523 | not applicable | not applicable |

This example illustrates the unexpected capability of this flow regime to approximate isothermal conditions in an adiabatic reactor system, and an unusual flexibility of temperature control within the reactor. The catalyst and solids recirculation and liquid feed and diluent act cooperatively and synergistically to achieve a low temperature differential within the reaction zone, thus permitting necessary adjustments to one variable to be offset by compensating adjustments to the other.

In the process of the present invention, the preferred oxygenates are methanol, dimethyl ether and mixtures thereof. The method of making the preferred olefin product in this invention can include the additional step of making the oxygenate compositions from hydrocarbons such as oil, coal, tar sand, shale, biomass and natural gas. Methods for making the compositions are known in the art. These methods include fermentation of biomass to alcohol or ether and also include making synthesis gas and then converting the synthesis gas to alcohol or ether. Synthesis gas can be produced by known processes such a steam reforming, autothermal reforming and partial oxidization.

One skilled in the art will appreciate that the olefins produced by the conversion reaction of the present invention can be polymerized to form polyolefins. Processes for forming polyolefins from olefins are known in the art. Catalytic processes are preferred. Particularly preferred are metallocene, Ziegler/Natta and acid catalytic systems. Prior to being subjected to a polymerization process, the olefin products are recovered from the products of the conversion reaction.

recovered therefrom. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore are not discussed here.

Persons of ordinary skill in the art will recognize that many modifications may be made to the present invention without departing from the spirit and scope of the present invention. The embodiments described herein are meant to be illustrative only and should not be taken as limiting the invention, which is defined by the following claims.

What is claimed is:

1. A method for converting a feed including an oxygenate to a product including a light olefin, said method comprising:

providing a feed including an oxygenate;

contacting said feed in a reaction zone of a reactor apparatus with a catalyst including a molecular sieve, said contacting taking place under conditions effective to convert said oxygenate to a product including a light olefin, said conditions including a gas superficial velocity of at least two meters per second at at least one point in said reaction zone; and recirculating a first portion of said catalyst to recontact said feed.

2. The method of claim 1 wherein said gas superficial velocity is greater than about 2.5 meters per second at at least one point in said reaction zone.

3. The method of claim 2 wherein said gas superficial velocity is greater than about 4 meters per second at at least one point in said reaction zone.

4. The method of claim 1 further including at least one step selected from a group consisting of the following: providing a portion of said feed to said reactor apparatus in a liquid form; providing non-reactive solids to said reactor apparatus; and providing a liquid diluent to said reactor apparatus.

5. The method of claim 4 wherein said at least one step controls a temperature differential in said reactor apparatus.

6. The method of claim 4 wherein said at least one step comprises providing non-reactive solids to said reactor apparatus and said method further includes the steps of removing a second portion of said catalyst and non-reactive solids from said reactor apparatus; regenerating at least a portion of said second portion of said catalyst and said non-reactive solids removed from said reactor apparatus to form a regenerated portion of catalyst and non-reactive solids; and returning said regenerated portion of said catalyst and said non-reactive solids to said reactor apparatus.

7. The method of claim 4 wherein said at least one step comprises providing a liquid diluent to said reactor apparatus at a plurality of positions on said reactor apparatus.

8. The method of claim 1 wherein said conditions further comprise a weight hourly space velocity of at least about 20 $hr^{-1}$.

9. The method of claim 1 wherein said oxygenate is selected from the group consisting of methanol; ethanol; n-propanol; isopropanol; $C_4$–$C_{10}$ alcohols; methyl ethyl ether; dimethyl ether; diethyl ether; di-isopropyl ether; methyl formate; formaldehyde; di-methyl carbonate; methyl ethyl carbonate, acetone; and mixtures thereof.

10. The method of claim 9 wherein said oxygenate is selected from the group consisting of methanol, dimethyl ether and mixtures thereof.

11. The method claim 1 wherein said molecular sieve is a silicoaluminophosphate molecular sieve.

12. The method of claim 1 further including the steps of: removing a second portion of said catalyst from said reactor apparatus; regenerating at least a portion of said second portion of said catalyst removed from said reactor apparatus to form a regenerated portion of catalyst; and returning said regenerated portion of catalyst to said reactor apparatus.

13. The method of claim 1 wherein said recirculating of said first portion of said catalyst maintains a temperature differential in said reaction zone at less than about 100° C.

14. The method of claim 13 wherein said recirculating of said first portion of said catalyst maintains said temperature differential in said reaction zone at less than about 50° C.

15. The method of claim 14 wherein said recirculating of said first portion of said catalyst maintains said temperature differential in said reaction zone at less than about 30° C.

16. The method of claim 4 wherein said portion of said feed in said liquid form is provided to said reactor apparatus at a plurality of positions on said reactor apparatus.

17. The method of claim 10 further including the step of forming said oxygenate.

18. The method of claim 1 further including the step of recovering said light olefin.

19. The method of claim 16 further including the step of polymerizing said light olefin to form a polymer.

20. The method of claim 18 further including the step of converting said light olefin into a light olefin derivative selected from the group consisting of aldehydes, alcohols, acetic acid, linear alpha olefins, vinyl acetate, ethylene dichloride, vinyl chloride, ethylbenzene, ethylene oxide, cumene, isopropyl alcohol, acrolein, allyl chloride, propylene oxide, acrylic acid, ethylene-propylene rubbers, acrylonitrile, trimers and dimers of ethylene, propylene, butylenes and mixtures thereof.

21. The method of claim 6 further including, prior to the step of returning said regenerated portion of said catalyst and said non-reactive solids to said reactor apparatus, the step of cooling said regenerated catalyst along and said non-reactive solids to a temperature which is from about 200° C. higher to about 200° C. lower than a temperature of said second portion of said catalyst and non-reactive solids removed from said reactor apparatus.

22. The method of claim 12 further including, prior to the step of returning said regenerated portion of said catalyst to said reactor apparatus, the step of cooling said at least a portion of said regenerated catalyst to a temperature which is from about 200° C. higher to about 200° C. lower than the temperature of said catalyst removed from said reactor apparatus.

23. A method for converting feed containing an oxygenate to a light olefin, said method comprising:

(a) providing a reactor apparatus having an inlet zone, a reaction zone and a disengaging zone, said reaction zone being positioned between said inlet zone and said disengaging zone;

(b) providing a feed including an oxygenate to said inlet zone;

(c) contacting said feed in said reaction zone with a catalyst including a molecular sieve, said contacting taking place under conditions effective to convert said oxygenate to a product including a light olefin, said conditions including a gas superficial velocity off at least two meters per second at at least one point in said reaction zone;

(d) separating said product from said catalyst in said disengaging zone;

(e) recirculating a first portion of said catalyst from said disengaging zone to said inlet zone; and (f) repeating steps (b) to (e).

24. The method of claim 23 wherein said gas superficial velocity is greater than about 2.5 meters per second at at least one point in said reaction zone.

25. The method of claim 24 wherein said gas superficial velocity is greater than 4 meters per second at at least one point in said reaction zone.

26. The method of claim 23 further including at least one step selected from the group consisting of the following: feeding a portion of said feed to said reactor apparatus in a liquid form; providing a non-reactive solid to said reaction zone; and providing a liquid diluent to said reaction zone.

27. The method of claim 26 wherein said at least one step controls a temperature differential in said reactor apparatus.

28. The method of claim 26 wherein said at least one step comprises providing non-reactive solids to said reactor apparatus and said method further includes the steps of removing a second portion of said catalyst and non-reactive solids from said reactor apparatus; regenerating at least a portion of said second portion of said catalyst and said non-reactive solids removed from said reactor apparatus to form a regenerated portion of said catalyst and said non-reactive solids; and returning said regenerated portion of said catalyst and said non-reactive olids to said reactor apparatus.

29. The method of claim 28 wherein said regenerated portion of said catalyst and non-reactive solids are returned to either said inlet zone, said reaction zone, or said disengaging zone.

30. The method of claim 26 wherein said at least one step comprises providing a liquid diluent to said reactor apparatus at a plurality of positions on said reactor apparatus.

31. The method of claim 23 wherein said conditions further comprise a weight hourly space velocity of at least about 20 $hr^{-1}$.

32. The method of claim 23 wherein said oxygenate is selected from the group consisting of methanol; ethanol; n-propanol; isopropanol; $C_4$–$C_{10}$ alcohols; methyl ethyl ether; dimethyl ether; diethyl ether; di-isopropyl ether; methyl formate; formaldehyde; di-methyl carbonate; methyl ethyl carbonate, acetone; and mixtures thereof.

33. The method of claim 32 wherein said oxygenate is selected from the group consisting of methanol, dimethyl ether and mixtures thereof.

34. The method of claim 23 wherein said molecular sieve is a silicoaluminophosphate molecular sieve.

35. The method of claim 23 further including the steps of: removing a second portion of said catalyst in said disengaging zone from said reactor apparatus; regenerating at least a portion of said second portion of said catalyst removed from said reactor apparatus to form a regenerated portion of catalyst; and returning said regenerated portion of said catalyst to said reactor apparatus.

36. The method of claim 35 wherein said regenerated portion of said catalyst is returned to either said inlet zone, said reaction zone, or said disengaging zone.

37. The method of claim 23 wherein said recirculating of said first portion of said catalyst maintains a temperature differential in said reaction zone at less than about 100° C.

38. The method of claim 37 wherein said recirculating of said first portion of said catalyst maintains said temperature differential in said reaction zone at less than about 50° C.

39. The method of claim 38 wherein said recirculating of said first portion of said catalyst maintains said temperature differential in said reaction zone at less than about 30° C.

40. The method of claim 26 wherein said portion of said feed in said liquid form is introduced to said reactor apparatus at a plurality of positions along said reactor apparatus.

41. The method of claim 33 further including the step of forming said oxygenate.

42. The method of claim 23 further including the step of recovering said light olefin.

43. The method of claim 42 further including the step of polymerizing said light olefin to form a polymer.

44. The method of claim 42 further including the step of converting said light olefin into a light olefin derivative selected from the group consisting of aldehydes, alcohols, acetic acid, linear alpha olefins, vinyl acetate, ethylene dichloride, vinyl chloride, ethylbenzene, ethylene oxide, cumene, isopropyl alcohol, acrolein, allyl chloride, propylene oxide, acrylic acid, ethylene-propylene rubbers, acrylonitrile, trimers and dimers of ethylene, propylene, butylenes and mixtures thereof.

45. The method of claim 35 further including, prior to the step of returning said regenerated portion of said catalyst to said reactor apparatus, the step of cooling said regenerated catalyst to a temperature which is from about 200° C. higher to about 200° C. lower than a temperature of said second portion of said catalyst removed from said reactor apparatus.

46. The method of claim 28 further including, prior to the step of returning said regenerated portion of said catalyst and said non-reactive solids to said reactor apparatus, the step of cooling said regenerated catalyst and said non-reactive solids to a temperature which is from about 200° C. higher to about 200° C. lower than a temperature of said second portion of said catalyst and said non-reactive solids removed from said reactor apparatus.

47. A method for converting a feed including an oxygenate to a product including a light olefin, said method comprising:
providing a feed including an oxygenate; and
contacting said feed in a reaction zone of a reactor apparatus with a catalyst including a non-zeolitic molecular sieve, said contacting taking place under conditions effective to convert said oxygenate to a product including a light olefin, said conditions including a gas superficial velocity of at least one meter per second at at least one point in said reaction zone.

48. The method of claim 47 wherein said non-zeolitic molecular sieve is a silicoaluminophosphate (SAPO).

49. The method of claim 49 wherein said gas superficial velocity is at least two meters per second at at least one point in said reaction zone.

50. The method of claim 49 wherein said gas superficial velocity is at least 2.5 meters per second at at least one point in said reaction zone.

51. The method of claim 50 wherein said gas superficial velocity is at least 4 meters per second at at least one point in said reaction zone.

52. The method of claim 47 further including the step of recirculating a first portion of said catalyst to recontact said feed.

53. The method of claim 52 further including at least one step selected from a group consisting of the following: providing a portion of said feed to said reactor apparatus in a liquid form; providing a non-reactive solid to said reactor apparatus; and providing a liquid diluent to said reactor apparatus.

54. The method of claim 53 wherein said at least one step controls a temperature differential in said reactor apparatus.

55. The method of claim 47 wherein said conditions further comprise a weight hourly space velocity of at least about 20 hr$^{-1}$.

56. The method of claim 47 wherein said oxygenate is selected from the group consisting of methanol; ethanol; n-propanol; isopropanol; $C_4$-$C_{10}$ alcohols; methyl ethyl ether; dimethyl ether; diethyl ether; di-isopropyl ether; methyl formate; formaldehyde; di-methyl carbonate; methyl ethyl carbonate, acetone; and mixtures thereof.

57. The method of claim 56 wherein said oxygenate is selected from th e group consisting of methanol, dimethyl ether and mixtures thereof.

58. The method of claim 47 further including the steps of: removing a second portion of said catalyst from said reactor apparatus; regenerating at least a portion of said second portion of said catalyst removed from said reactor apparatus to form a regenerated portion of catalyst; and returning said regenerated portion of said catalyst to said reactor apparatus.

59. The method of claim 53 wherein said at least one step comprises providing non-reactive solids to said reactor apparatus and said method further includes the steps of removing a second portion of said catalyst and non-reactive solids from said reactor apparatus; regenerating at least a portion of said second portion of said catalyst and said non-reactive solids removed from said reactor apparatus to form a regenerated portion of said catalyst and said non-reactive solids; and returning said regenerated portion of said catalyst and said non-reactive solids to said reactor apparatus.

60. The method of claim 59 further including, prior to the step of returning said regenerated portion of said catalyst and said nonreactive solids to said reactor apparatus, the step of cooling said regenerated catalyst and said non-reactive solids to a temperature which is from about 200° C. higher to about 200° C. lower than a temperature of said second portion of said catalyst and said non-reactive solids removed from said reactor apparatus.

61. The method of claim 53 wherein said at least one step comprises providing a liquid diluent to said reactor apparatus at a plurality of positions on said reactor apparatus.

62. The method of claim 52 wherein said recirculating of said first portion of said catalyst maintains a temperature differential in said reaction zone at less than about 100° C.

63. The method of claim 62 wherein said recirculating of said first portion of said catalyst maintains said temperature differential in said reaction zone apparatus at less than about 50° C.

64. The method of claim 63 wherein said recirculating of said first portion of said catalyst maintains said temperature differential in said reaction zone at less than about 30° C.

65. The method of claim 53 wherein said portion of said feed in said liquid form is provided to said reactor apparatus at a plurality of positions on said re actor apparatus.

66. The method of claim 47 further including the step of forming said oxygenate.

67. The method of claim 47 further including the step of recovering said light olefin.

68. The method of claim 67 further including the step of polymerizing said light olefin to form a polymer.

69. The method of claim 67 further including the step of converting said light olefin into a light olefin derivative selected from the group consisting of aldehydes, alcohols, acetic acid, linear alpha olefins, vinyl acetate, ethylene dichloride, vinyl chloride, ethylbenzene, ethylene oxide, cumene, isopropyl alcohol, acrolein, allyl chloride, propylene oxide, acrylic acid, ethylene-propylene rubbers, acrylonitrile, trimers and dimers of ethylene, propylene, butylenes and mixtures thereof.

70. The method of claim 58 further including, prior to the step of returning said regenerated portion of said catalyst to said reactor apparatus, the step of cooling said at least a portion of said regenerated catalyst to a temperature which is from about 200° C. higher to about 200° C. lower than the temperature of the catalyst removed from said reactor apparatus.

* * * * *